United States Patent
Murphy

(10) Patent No.: US 7,037,310 B2
(45) Date of Patent: May 2, 2006

(54) ACETABULAR IMPACTOR

(75) Inventor: Stephen B. Murphy, Medford, MA (US)

(73) Assignee: Wright Medical Technology Inc, Arlington, TN (US)

( * ) Notice: Subject to any disclaimer, the term of this patent is extended or adjusted under 35 U.S.C. 154(b) by 0 days.

(21) Appl. No.: 10/691,143

(22) Filed: Oct. 21, 2003

(65) Prior Publication Data

US 2005/0085823 A1  Apr. 21, 2005

(51) Int. Cl.
*A61B 17/60* (2006.01)
(52) U.S. Cl. ....................................... 606/91
(58) Field of Classification Search .................. 606/81, 606/91, 99, 100; 623/22.21–39
See application file for complete search history.

(56) References Cited

U.S. PATENT DOCUMENTS

| | | | |
|---|---|---|---|
| 3,685,058 A | 8/1972 | Tronzo | |
| 3,859,992 A | 1/1975 | Amstutz | |
| 3,874,003 A | 4/1975 | Moser et al. | |
| 4,305,394 A * | 12/1981 | Bertuch, Jr. | 606/91 |
| 4,399,813 A | 8/1983 | Barber | |
| 4,475,549 A * | 10/1984 | Oh | 606/91 |
| 4,528,980 A | 7/1985 | Kenna | |
| 4,632,111 A | 12/1986 | Roche | |
| 4,662,891 A | 5/1987 | Noiles | |
| 4,677,972 A | 7/1987 | Tornier | |
| 4,716,894 A | 1/1988 | Lazzeri et al. | |
| 4,878,918 A | 11/1989 | Tari et al. | |
| 4,994,064 A | 2/1991 | Aboczsky | |
| 5,030,221 A | 7/1991 | Buechel et al. | |
| 5,037,424 A | 8/1991 | Aboczsky | |
| 5,061,270 A | 10/1991 | Abocszky | |
| 5,098,437 A | 3/1992 | Kashuba et al. | |
| 5,108,448 A | 4/1992 | Gautier | |
| 5,108,452 A | 4/1992 | Fallin | |
| 5,116,339 A | 5/1992 | Glock | |
| D331,461 S | 12/1992 | Lester | |
| 5,167,399 A | 12/1992 | Ryland et al | |
| 5,169,399 A * | 12/1992 | Ryland et al. | 606/91 |
| 5,171,243 A | 12/1992 | Kashuba et al. | |
| 5,171,313 A | 12/1992 | Salyer | |
| 5,190,422 A | 3/1993 | Lechot | |
| 5,217,499 A | 6/1993 | Shelley | |
| 5,250,051 A | 10/1993 | Maryan | |
| 5,261,915 A | 11/1993 | Durlacher et al. | |
| 5,284,483 A * | 2/1994 | Johnson et al. | 606/86 |
| 5,320,625 A | 6/1994 | Bertin | |
| 5,344,461 A | 9/1994 | Philpot | |
| 5,364,403 A | 11/1994 | Petersen et al. | |
| 5,417,696 A | 5/1995 | Kashuba | |
| 5,458,637 A | 10/1995 | Hayes | |
| 5,474,560 A * | 12/1995 | Rohr, Jr. | 606/91 |

(Continued)

FOREIGN PATENT DOCUMENTS

EP  0147339 A2  7/1985

(Continued)

OTHER PUBLICATIONS

Murphy, Minimally Invasive Hip Surgery, From www.stephensmurphy.com (2003).

(Continued)

*Primary Examiner*—Eduardo Robert
*Assistant Examiner*—Annette Reimers

(57) ABSTRACT

An improved acetabular impactor, especially suitable for use in minimally invasive hip surgeries, is disclosed. The impactor is simple in design and operation and spatially optimized. In particular, the impactor is designed to remotely detach the acetabular shell from the impactor via different potential mechanical connections.

20 Claims, 5 Drawing Sheets

U.S. PATENT DOCUMENTS

| | | | |
|---|---|---|---|
| 5,486,181 A | 1/1996 | Cohen et al. | |
| 5,499,985 A | 3/1996 | Hein et al. | |
| 5,507,748 A | 4/1996 | Sheehan et al. | |
| 5,584,837 A * | 12/1996 | Petersen | 606/91 |
| 5,658,290 A | 8/1997 | Lechot | |
| 5,658,294 A * | 8/1997 | Sederholm | 606/91 |
| 5,683,399 A * | 11/1997 | Jones | 606/91 |
| 5,904,688 A | 5/1999 | Gilbert | |
| 5,928,287 A | 7/1999 | Keller | |
| 5,968,049 A | 10/1999 | DaRold | |
| 6,063,123 A | 5/2000 | Burrows et al. | |
| 6,063,124 A | 5/2000 | Amstutz | |
| 6,106,536 A | 8/2000 | Lechot | |
| 6,129,732 A | 10/2000 | Lechot | |
| 6,132,469 A | 10/2000 | Schroeder | |
| 6,264,647 B1 | 7/2001 | Lechot | |
| 6,482,209 B1 | 11/2002 | Engh et al. | |
| 6,626,913 B1 | 9/2003 | McKinnon et al. | |
| 2001/0006593 A1 | 7/2001 | Lechot | |
| 2002/0002365 A1 | 1/2002 | Lechot | |
| 2002/0010470 A1 | 1/2002 | Lechot | |
| 2002/0099447 A1 | 7/2002 | Mears et al. | |
| 2002/0116067 A1 | 8/2002 | Mears et al. | |
| 2002/0193797 A1 | 12/2002 | Johnson et al. | |
| 2003/0004513 A1 | 1/2003 | Guzman et al. | |
| 2003/0050645 A1 | 3/2003 | Parker et al. | |
| 2003/0097135 A1 | 5/2003 | Penenberg | |
| 2003/0158559 A1 | 8/2003 | Diaz | |
| 2003/0181916 A1 | 9/2003 | Wolford | |
| 2003/0220696 A1 | 11/2003 | Mears et al. | |
| 2003/0229352 A1 | 12/2003 | Penenberg | |
| 2003/0229356 A1 | 12/2003 | Dye | |
| 2003/0229357 A1 | 12/2003 | Dye | |

FOREIGN PATENT DOCUMENTS

| | | |
|---|---|---|
| EP | 0357270 A1 | 3/1990 |
| EP | 0470912 A2 | 2/1992 |
| EP | 1149562 A2 | 10/2002 |
| EP | 1149562 A3 | 1/2003 |
| GB | 2372707 A | 9/2002 |
| WO | WO03/057049 A1 | 7/2003 |
| WO | WO03/065906 A2 | 8/2003 |

OTHER PUBLICATIONS

Author unknown. Short External Rotator Muscles of the Hip. From www.biyee.net/running/injury/short_rotators.html (2002).

Precimed tool advertisement (2002).

Minimally Invasive Hip Surgery and Future Developments, From www.essexhipsurgeon.co.uk/minimally_invasive_hip_replacement_surgery.html (2003).

Innomend MIS catalog (2003.

McTighe, A New Era of Minimally Invasive Surgical Approaches for THA, Joint Implant Surgery & Research Foundation Update (Dec., 2002).

Berry, et al. Symposium on Minimally Invasive THA, J. Bone Joint Surg. 85A: 2235-2246 (2003).

Pellegrini, et al., Surgical Approaches to the Hip Joint. In: Surgery of the Musculoskeletal System (C. M. Evarts, Ed.), Churchill Livingstone (New York, NY) Chapter 94, pp. 2735-2756 (1990).

* cited by examiner

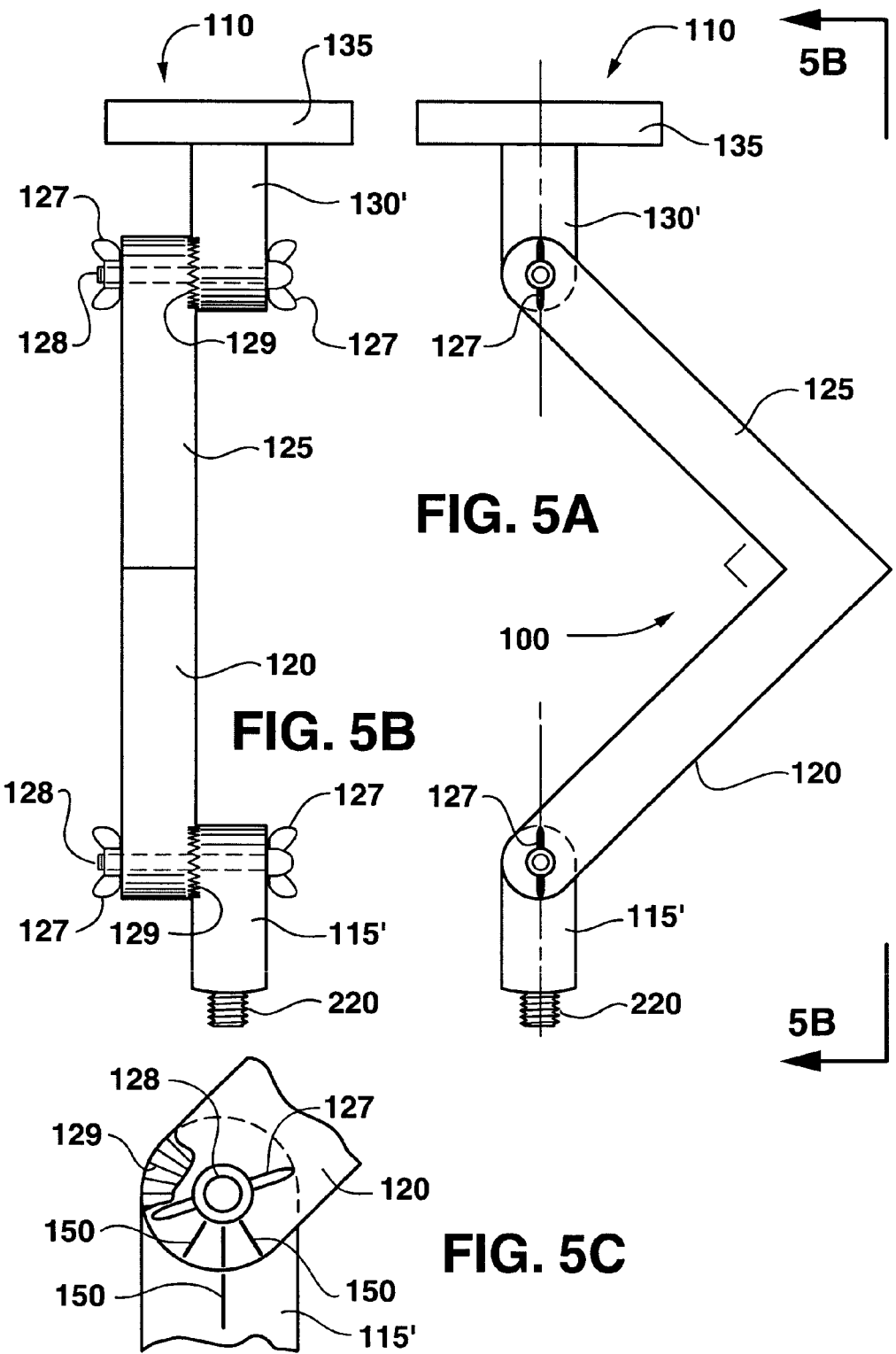

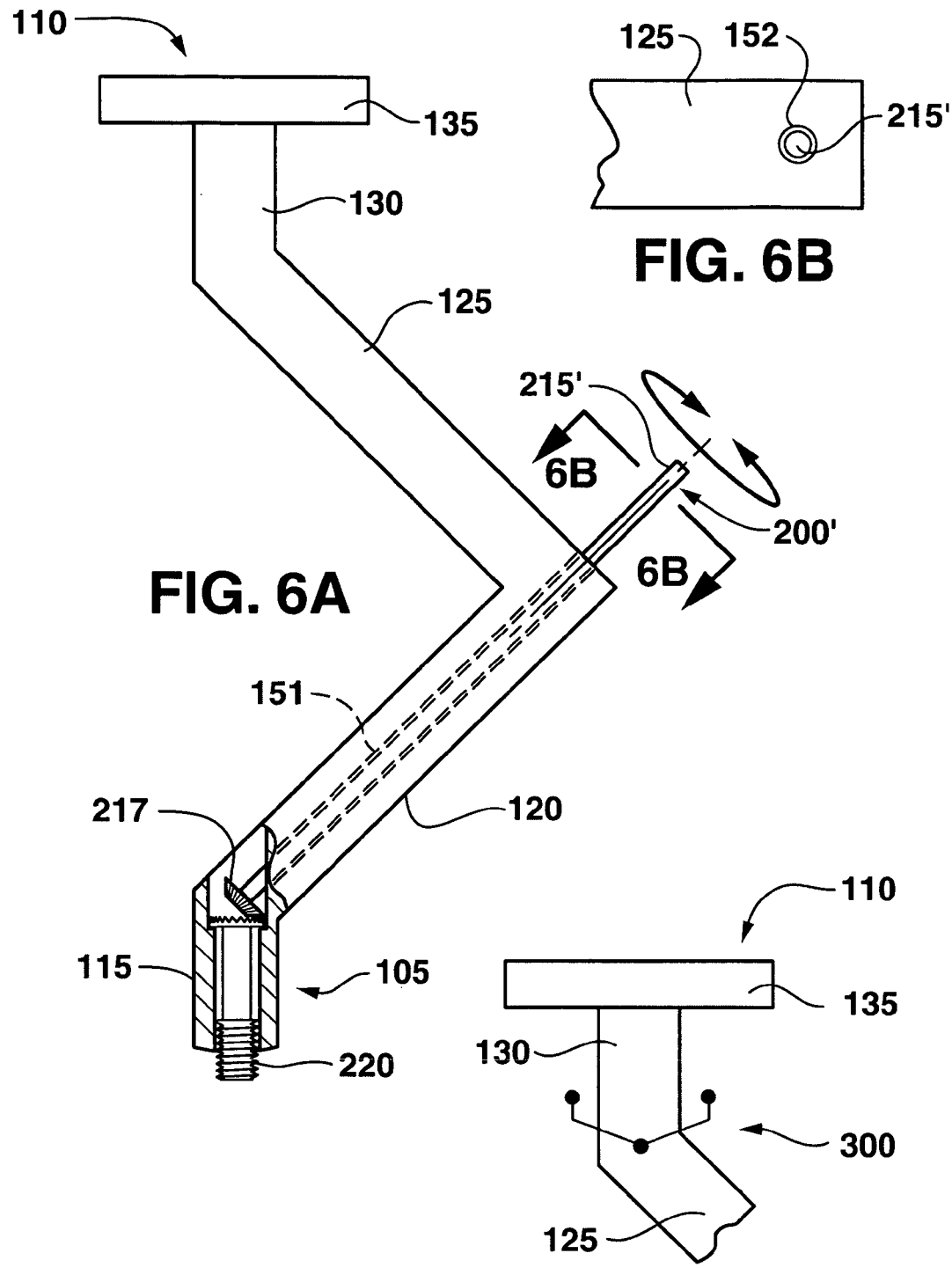

ACETABULAR IMPACTOR

RELATED APPLICATIONS

This application is related to assignee's U.S. patent application Ser. No. 10/691,800, filed [concurrently with this application].

FIELD OF THE INVENTION

This invention is generally directed to the field of hip arthroplasty. The invention is specifically directed to an improved acetabular impactor, especially suitable for use in minimally invasive hip surgeries.

BACKGROUND OF THE INVENTION

Traditionally, hip replacement surgery has been done via "open" surgical procedures. With open procedures, space for inserting and manipulating surgical instruments is not that critical and it is easier to get around major anatomical features, such as the greater trochanter of the femur.

However, with the advent of minimally-invasive surgical procedures for hip replacement, small incision sizes combined with tight anatomical clearances have resulted in the need for surgical instruments that take maximum availability of available space.

Exemplary instruments specifically described as being designed for MIS surgeries are shown in, for example, U.S. Pub. 2003/0050645 (Parker et al), U.S. Pub. 2003/0158559 (Diaz), and W003/065906 (Chana). Another device that appears to be at least designed with an eye towards MIS issues is shown in U.S. Pat. No. 5,474,560 (Rohr). However, as shown in Rohr's drawings, its bulging arcuate portion 16 does not seem to extend far enough out to provide a good working clearance for the greater trochanter.

All patents and publications mentioned herein are incorporated by reference herein.

While these devices may be acceptable for their intended or described uses, they are often complex and not geometrically and spatially optimized. Accordingly, there is room for improvement within the art.

SUMMARY OF THE INVENTION

It is an object of the invention to provide an improved acetabular impactor.

It is an object of the invention to provide an improved acetabular impactor especially suitable for use in minimally invasive surgical procedures.

It is an object of the invention to provide an improved acetabular impactor that is simple in design and operation.

It is an object of the invention to provide an improved acetabular impactor that is spatially optimized.

These and other objects of the invention are achieved by an acetabular shell impactor, comprising: an impactor body having first and second ends; a releasable connection for attaching an acetabular shell to the impactor; a remote actuator for releasing the connection between the shell and the impactor; and the remote actuator manipulated distant the first and second ends.

These and other objects of the invention are also achieved by an acetabular impactor, comprising: first and second ends; the first end for receiving an impact of a hammering device; the second end having a connection for attaching an acetabular shell thereto, the connection having an attachment axis; a first leg extending from the connection and parallel to the attachment axis; a second leg, acutely angled with respect to the first leg, and extending from the first leg; a third leg, extending at an angle with respect to the second leg; and a fourth leg, acutely angled with respect to the third leg, and extending parallel and opposite to the first leg.

These and other objects of the invention are yet also achieved by an acetabular impactor, comprising: first and second ends; the first end for receiving an impact of a hammering device; the second end having a connection for attaching an acetabular shell having an inner radius thereto; a first leg extending from the connection and parallel to the attachment axis; a second leg, acutely angled with respect to the first leg, and extending from the first leg; the length of the first leg is less than the inner radius.

BRIEF DESCRIPTION OF THE DRAWINGS

FIGS. 5A, 5B and 5C depict various views of an alternative exemplary embodiment of an acetabular impactor according to the invention.

FIG. 6A depicts a second alternative exemplary embodiment of an acetabular impactor according to the invention.

FIG. 6B is a view along line 6B—6B of FIG. 6A.

FIG. 7 depicts an embodiment of an acetabular impactor according to the invention configured for use with surgical navigation assistance.

DETAILED DESCRIPTION OF THE DRAWINGS

With reference to the drawings, various exemplary embodiments of an acetabular impactor that meets and achieves the various objects of the invention set forth above will now be described.

Figure 1:
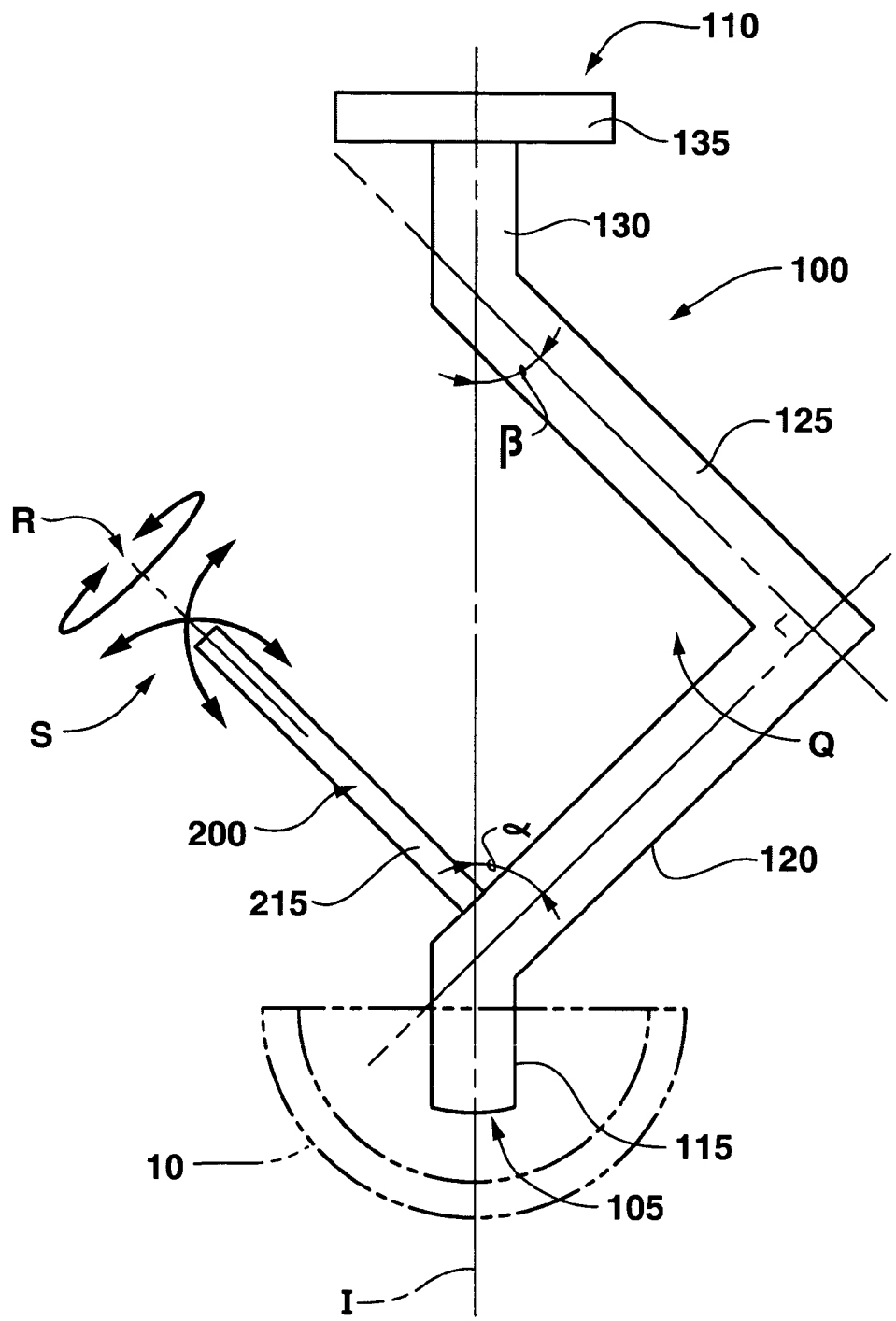
FIG. 1 depicts an exemplary embodiment of an acetabular impactor according to the invention.

FIG. 1 depicts an exemplary embodiment of an acetabular impactor according to the invention. The acetabular impactor is especially suitable for use in minimally invasive surgery ("MIS"). During MIS, typically an incision size of less than 8 cm will be made. Furthermore, if there is no dislocation of the hip joint during the surgery, available space for surgical instruments will be even further limited. During MIS hip procedures, having acetabular reaming and impacting instruments avoid the greater trochanter becomes critical in the tight space available to the surgeon.

The acetabular impactor 100 generally comprises first and second opposite ends. The first end comprises an impact end 110, which will typically be hit by an impacting tool (not shown), such as a mallet or hammer, as described in any of the references previously cited above. The second end comprises an attachment end 105 for attaching an acetabular shell 10 to the acetabular impactor 100.

Figure 3:
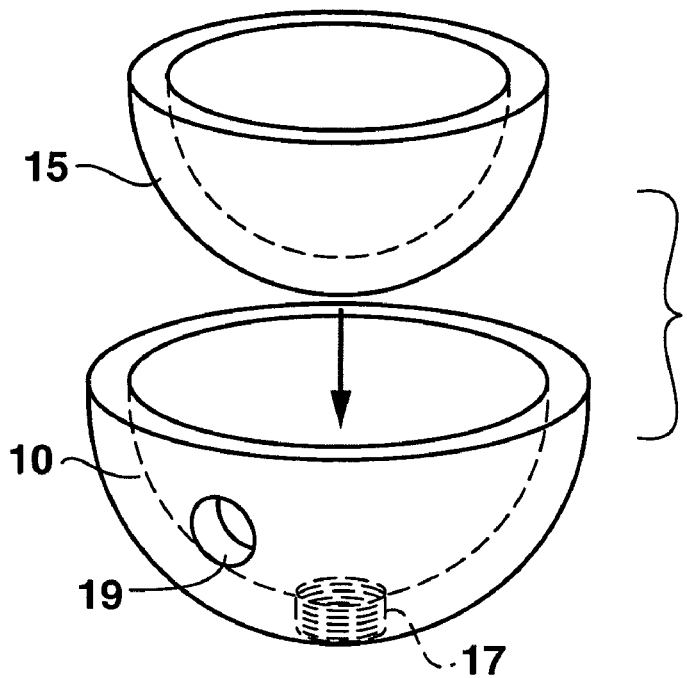
FIG. 3 depicts an exemplary acetabular shell and liner for use with the acetabular impactor according to the invention.

By way of background, FIG. 3 depicts an exemplary acetabular shell 10 and liner 15 for use with the acetabular impactor 100 according to the invention. An acetabular shell 10 is the portion of the implant that is directly implanted in the natural acetabulum of the patient undergoing hip replacement surgery. Acetabular shell 10 has a threaded hole 17 at its bottom for attachment to an impacting device such as shown in the invention. After the shell 10 is implanted, a shell liner 15, most typically made from either: metal, ceramic, or polyethylene (e.g. UHMWPE), is then inserted into the acetabular shell 10, as shown by the arrow. For situations in which additional fixation between the acetabular shell 10 and the patient's natural acetabulum is required, screws (not shown), may be passed through one or more screw holes 19 in shell 10 and into the bone surrounding the acetabulum. The patient's acetabulum would now be ready for receipt of the femoral portion, e.g., femoral head, of the implant.

Getting back to the acetabular impactor 100, impact end 110 will typically have an impact surface 135 for direct receipt of the blows of the impacting tool. Between attachment end 105 and impact end 110, is the body of acetabular impactor 100. The body of acetabular impactor 100 generally comprises four legs straight, 115, 120, 125, and 130. Straight legs are preferred, of, U.S. Pub. to Parker, supra, because sometimes the legs of the acetabular impactor will also be struck by the impacting tool during impaction to set up valgus and varus and straight legs make sure the impact is squarely applied to the acetabular impactor 100. First leg 115 and fourth leg 130 are at least parallel and typically coaxial along the impact axis I. Second leg 120 will typically extend at an angle a from first leg 115. Angle α will typically be an acute angle, and most preferably 45 degrees. Third leg 125 will typically be fixed with respect to the second leg 120, preferably at a right angle (however, curves are feasible in this narrow area). Second and third legs 120 and 125 are preferred to each be about 7 inches long. Finally, fourth leg 130 will typically extend at an angle β from first third 125. Angle β will typically be an acute angle and equal to angle α, e.g., most preferably 45 degrees. When this preferred leg configuration is applied, an open area Q will result that is spatially optimized for fitting in of the greater trochanter of the femur (not shown) during an acetabular impaction.

Finally, impactor 100 has a remote actuator 200 for remotely releasing the acetabular shell 10 from the attachment end 105 of acetabular impactor 100. By "remotely", it is meant that the release may be achieved without the surgeon having to reach into the incision site. Actuator 200 includes a rotatable actuation rod 215. Rotation R may be either manual or by any powered means (not shown). As will be described below, actuation rod 215 can swing in various directions as depicted by the arrows S to make manipulation of actuation rod 215 easier. Though in FIG. 1 actuation rod 215 is shown in area Q, the area for anatomical features such as the greater trochanter, this is for illustration purposes only. When impactor 100 is actually used, actuation rod 215 will be swung out of area Q leaving that area fully open for its intended use.

Figure 2A:
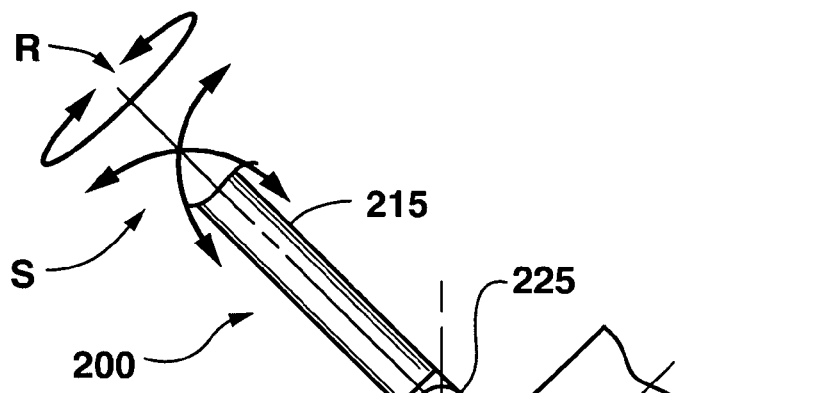
FIG. 2A depicts an exemplary releasable connection between an acetabular shell and an acetabular impactor according to an exemplary embodiment of the invention.

FIG. 2A depicts an exemplary releasable connection between an acetabular shell 10 and an acetabular impactor 100 according to an exemplary embodiment of the invention.

As shown in FIG. 2A, typically first leg 115 will be hollow and contain therein a threaded rod, machine screw, or threaded stud 220. The threads of threaded stud 220 will correspond to those of the threaded hole 17 of the acetabular shell 10 so that acetabular shell 10 may be attached thereto.

Figure 2B:
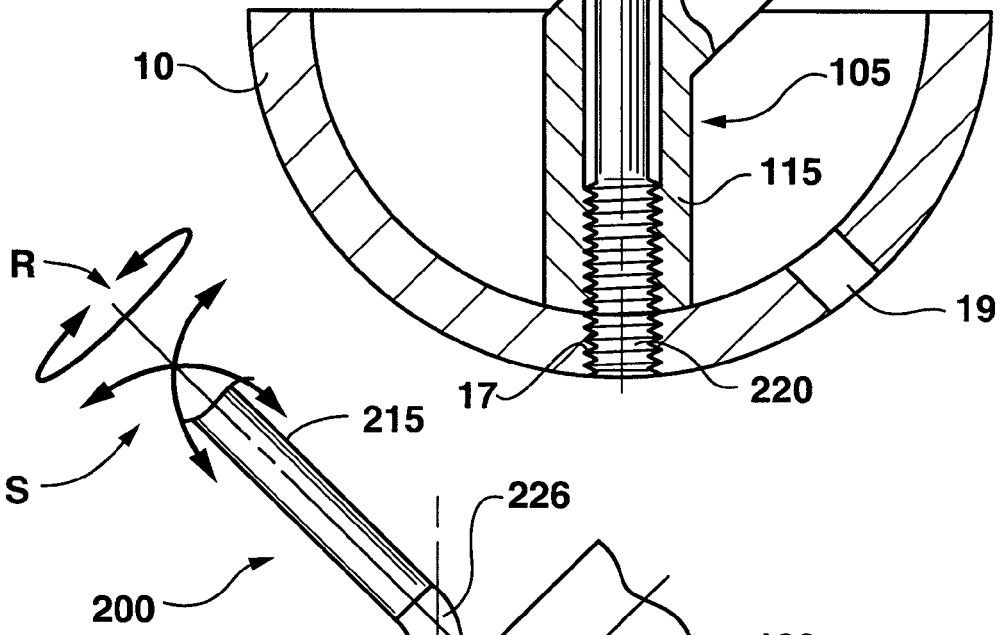
FIG. 2B depicts an alternative exemplary releasable connection between an acetabular shell and an acetabular impactor according to an exemplary embodiment of the invention.

Attached to threaded stud 220 will be a mechanical linkage or any other physical attachment capable of converting the rotation R of actuation rod 215 from along whatever rotational axis actuation rod 215 may be on to that of threaded stud 220. While the preferred physical attachment may comprise a universal-joint 225, the invention is not so limited. For example, a solid flexible coupling 226 (FIG. 2B) may be used or a bevel gear mechanism (FIGS. 6A, 6B).

The exemplary releasable connection works as follows. After the acetabular shell 10 has been impacted in a prepared natural acetabulum, it will be tightly positioned therein and therefore prevented from rotating without the application of excessive force/torque. Accordingly, upon rotation of actuation rod 215, threaded stud 220 will rotate itself out of threaded hole 17 of acetabular shell 10 until the acetabular shell 10 becomes separated from acetabular impactor 100. Acetabular impactor 100 is then removed from the incision site.

Figure 4:
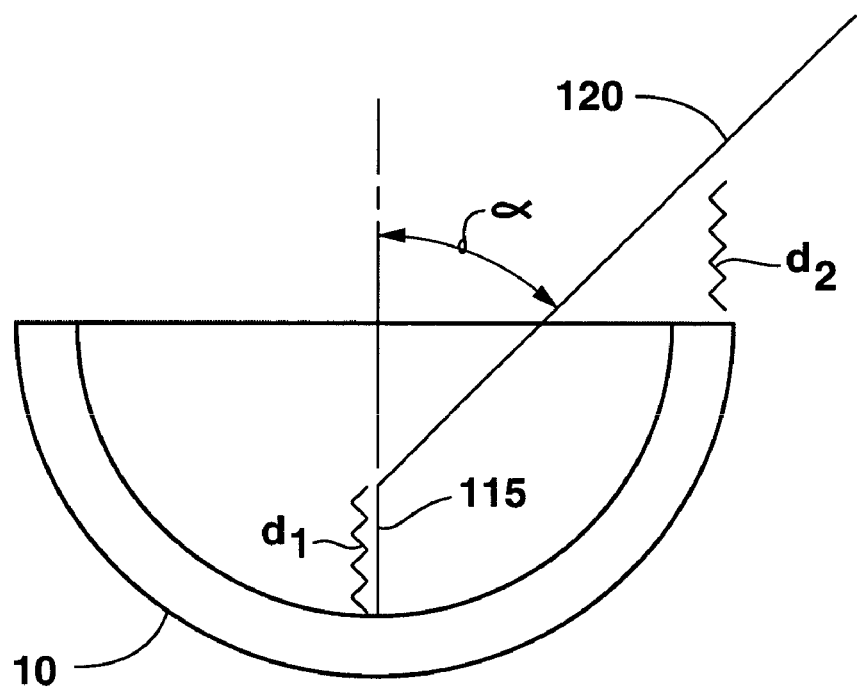
FIG. 4 depicts the preferred correlation between the lengths of the various legs of an exemplary impactor according to the invention.

FIG. 4 depicts the preferred correlation between the lengths of various legs of an exemplary acetabular impactor 100 according to the invention. These lengths become important when considering the fact that the instrument must fit within a tightly confined area when conducting MIS hip surgery. In general, according to the invention, the length d1 of first leg 115 should be, when taking into account the selected angle α, just enough to cause a slight clearance d2 (e.g. no impingement) between second leg 120 and the rim of acetabular shell 10, as the second leg 120 extends out passed the rim circumference of acetabular shell 10. This length d1 will typically be less than the inner diameter of acetabular shell 10. Furthermore, while as mentioned above, second leg 120 will typically and preferably be about 7 inches, it will at least be greater than the inner radius of the acetabular shell 10.

FIGS. 5A, 5B, and 5C depict various views of an alternative exemplary embodiment of an acetabular impactor according to the invention in which actuation rod 215 is omitted merely for clarity. In this alternative embodiment, the angle α between first leg 115' and second leg 120 and the angle β between third leg 125 and fourth leg 130' can both be varied. This is achieved by first making first leg 115' and fourth leg 130' separate members from second leg 120 and third leg 125, which may be left as a unitary, or at least integral member. The various members are connected for relative movement by using, for example, threaded members 128 and wing bolts 127, for ease of manipulation, e.g., without need for tools. Additionally, it is possible to provide the inner walls (e.g., those that come into contact with each other) of the various members with mating teeth or serrations 129 such that when the acetabular impactor is hit by the impacting tool, it becomes much harder for the angles to change from those selected. As shown in FIG. 5C, markings 150 can be placed on one or more of the various legs to assist the surgeon in setting the legs to the desired or predetermined angles.

FIGS. 6A and 6B depict a second alternative exemplary embodiment of an acetabular impactor 100 according to the invention. In this second alternative exemplary embodiment, actuation rod 215' is shown as passing through a hollow channel 151 in second leg 120 and protruding from acetabular impactor 100 through a hole 152 in third leg 125. Furthermore, this embodiment is shown with yet another alternative physical attachment between actuation rod 215' and threaded stud 220. Optional bevel gear drive 217 is mounted on the end of actuation rod 215'. Through this rigid bevel gear connection, it is predicted that this embodiment may be the most robust in regards to resisting the impact stressed to which the impactor 100 is subjected. However, as previously mentioned, any mechanical coupling may be used, as in the other exemplary embodiments of the invention.

Acetabular impactor 100 has been so far described above with respect to a non-surgical navigation assisted device. However, as shown in FIG. 7, it is extremely easy to add navigation markers 300 or other alignment means to any portion of the acetabular impactor, for example, close to the impaction end 110 for use in setting varus, valgus, and leg length with an external camera and navigation system. A detailed description of surgical navigation or the various types of alignment means available are beyond the scope of this application but well known in the art.

While the invention has been described with relation to certain proposed exemplary and preferred embodiments, the invention is not so limited. Reference should be made to the claims when assessing the scope of the true invention.

The invention claimed is:

1. An acetabular impactor, comprising:
   an impactor body having first and second ends;
   a releasable connection for attaching an acetabular shell to said impactor;
   a remote actuator for releasing the connection between said shell and said impactor;
   said remote actuator manipulated distant said first and second ends, and
   said actuator including a mechanical drive, wherein said mechanical drive can transfer rotational motion from one axis to another.

2. The acetabular impactor according to claim 1, wherein:
   said remote actuator is swingable independent of said impactor body.

3. The acetabular impactor according to claim 1, wherein said mechanical drive includes a universal-joint.

4. The acetabular impactor according to claim 1, wherein said mechanical drive includes a bevel gear.

5. The acetabular impactor according to claim 1, wherein at least a portion of the actuator is within said body.

6. The acetabular impactor according to claim 5, wherein said body is rigid.

7. The acetabular impactor according to claim 1, wherein said releasable connection comprises a threaded connection.

8. The acetabular impactor according to claim 1, wherein:
   said first end for receiving an impact of a hammering device;
   said second end having said connection for attaching an acetabular shell thereto, said connection having an attachment axis;
   a first leg extending from said connection and parallel to said attachment axis;
   a second leg, acutely angled with respect to said first leg, and extending from said first leg;
   a third leg, extending at an angle with respect to said second leg; and
   a fourth leg, acutely angled with respect to said third leg, and extending parallel and opposite to said first leg.

9. The acetabular impactor of claim 8, wherein the angle between said second and third legs is a right angle and said second and third legs are substantially the same length.

10. The acetabular impactor of claim 9, wherein said legs are rigid and of a fixed length.

11. The acetabular impactor of claim 10, wherein said first and fourth legs are coaxial.

12. The acetabular impactor of claim 9, wherein said acute angles may be varied.

13. The acetabular impactor of claim 12, wherein said first and fourth legs are separate members from said second and third legs, and wherein said acute angles may be varied by varying the angles between said separate legs.

14. The acetabular impactor of claim 8, wherein:
   said shell has an inner radius; and
   the length of said first leg is less than said inner radius.

15. The acetabular impactor of claim 14, wherein said length of said first leg being the smallest length that does not cause impingement of said shell and said second leg.

16. The acetabular impactor of claim 14, wherein the length of said second leg is greater than said inner radius.

17. The acetabular impactor of claim 8, further comprising a navigation frame.

18. The acetabular impactor according to claim 8, wherein said releasable connection comprises a threaded connection.

19. The acetabular impactor according to claim 1, wherein:
   said first end for receiving an impact of a hammering device;
   said second end having said connection for attaching an acetabular shell, said acetabular shell having an inner radius thereto;
   a first leg extending from said connection and parallel to said attachment axis;
   a second leg, acutely angled with respect to said first leg, and extending from said first leg;
   the length of said first leg is less than said inner radius.

20. The acetabular impactor according to claim 1, wherein said mechanical drive is a solid flexible coupling.

* * * * *